United States Patent [19]

Kato et al.

[11] 4,413,148
[45] Nov. 1, 1983

[54] PROCESS FOR PRODUCING DICUMYLPEROXIDE

[75] Inventors: Mitsukuni Kato; Takuya Demachi; Hidehiko Hagii; Takeshi Arai, all of Aichi, Japan

[73] Assignee: Nippon Oil and Fats Co., Ltd., Tokyo, Japan

[21] Appl. No.: 349,413

[22] Filed: Feb. 16, 1982

[30] Foreign Application Priority Data

Feb. 19, 1981 [JP] Japan .................................. 56-23526

[51] Int. Cl.$^3$ ................ C07C 179/035; C07C 179/06
[52] U.S. Cl. .................................................... 568/578
[58] Field of Search ....................................... 568/578

[56] References Cited

U.S. PATENT DOCUMENTS

| | | | |
|---|---|---|---|
| 2,668,180 | 2/1954 | Boardmann | 568/578 |
| 3,310,588 | 3/1967 | Kloosterman et al. | 568/578 |
| 3,337,639 | 8/1967 | Stedehouser et al. | 568/578 |
| 4,198,528 | 4/1980 | Kelsey | 568/578 |
| 4,266,081 | 5/1981 | Mizuno et al. | 568/578 |

FOREIGN PATENT DOCUMENTS

| | | | |
|---|---|---|---|
| 37-10668 | 8/1962 | Japan | 568/578 |
| 38-2265 | 7/1963 | Japan | 568/578 |
| 792558 | 6/1956 | United Kingdom | 568/578 |
| 896813 | 5/1962 | United Kingdom | 568/578 |

OTHER PUBLICATIONS

Japanese Patent Publication No. 1 6719/1962 and English Translation of Claim 1 thereof
Japanese Patent Publication No. 2 7240/1964 and English Translation of Claim 1 thereof

*Primary Examiner*—Werren B. Lone
*Attorney, Agent, or Firm*—Flynn, Thiel, Boutell & Tanis

[57] ABSTRACT

In a process for producing a dicumyl peroxide comprising reacting a cumene hydroperoxide and an α,α-dimethylbenzyl alcohol in the presence of an acid catalyst, when a polar solvent exists in the reaction system, the cumene hydroperoxide of the starting material and the dicumyl peroxide of the resulting product are scarcely decomposed.

6 Claims, No Drawings

PROCESS FOR PRODUCING DICUMYLPEROXIDE

BACKGROUND OF THE INVENTION

FIELD OF THE INVENTION

This invention relates to an improved process for producing dicumylperoxide.

Hithertofore, there have been known processes for producing dicumylperoxide (hereinafter refered to as DCP), in which cumene hydroperoxide (hereinafter refered to as CHP) and α,α-dimethylbenzyl alcohol (hereinafter refered to as α-CA) are reacted. These processes are as follows: (1) A process characterized in that a strong acid such as sulfuric acid, perchloric acid, p-toluenesulfonic acid, a cation exchange resin, or the like is used as the catalyst in a reaction system (Japanese Patent Publication Nos. 10668/1962 and 2265/1963, U.S. Pat. No. 2,668,180 and British Pat. No. 792,558); (2) A process characterised in that the reaction is carried out using a lesser amount of the strong acid catalyst, while removing the water which formed in the reaction system therefrom under reduced pressure (Japanese Patent Publication No. 16719/1962); (3) A process characterized in that an oxalic anhydride is used for the reaction as the acid catalyst and a dehydrating agent (Japanese Patent Publication No. 27240/1964); (4) A process characterized in that potassium bisulfate or the like, which is a weak acid, instead of the above stated strong acid catalyst, is used for the reaction, while introducing an inactive gas in the reaction system (Japanese Patent Publication No. 12374/1960).

However, ranges of the optimum usage amount of the catalyst and of the reaction temperature in the process (1) are narrow because CHP and DCP are easily decomposed by the strong acid, and the process gives a low yield under the usual reaction conditions.

The process (2), in which the range of optimum usage amount of sulfuric acid is also narrow, needs a complex installation in order to carefully maintain the optimum reaction temperature and the reaction pressure while removing the water formed in the reaction system from the reaction system by distillation.

The process (3) involves the possibility of decomposition of DCP. because anhydrous oxalic acid is a strong acid and further is used in a large amount.

For these reasons there is a drawback in that the reaction should be carried out for a long time, while maintaining the reaction temperature at about 40° C.

In addition, oxalic acid is strongly poisonous and exerts large corrosion activity on metals.

For the process (4), for which the reaction rate is slow, it is necessary to raise the reaction temperature up to about 90° C.

It is not preferable to obtain a peroxide, which is apt to undergo thermal decomposition at such a high temperature.

Especially, it is dangerous to produce the peroxide in an industrial scale production according to the process (4), because the resulting peroxide is kept at such a high temperature as stated above, with the result being that an abnormal reaction happens in the reaction system and cause an explosion.

As mentioned above, the conventional processes for producing DCP by the reaction of CHP and α-CA are either one in which the reaction is carried out under strict restrictions using a strongly acidic catalyst or ones in which the reaction is carried out at a high temperature using a weak acid catalyst.

Neither process is preferable as an industrial scale production process in view of the yield and safety.

SUMMARY OF THE INVENTION

This invention aims to provide a process for producing DCP in high yield, in safety and further at a moderate cost.

This invention is based on the findings that in a process for producing a dicumylperoxide which comprises reacting CHP and α-CA in the presence of an acid catalyst, while removing continuously water which is formed in the reaction, from the reaction system, when the reaction is carried out in the presence of a polar solvent, the starting material CHP and the reaction product are scarcely decomposed even though the catalyst is a strong acid.

According to this invention, DCP is prepared by a method which is characterized in that, in a process for producing DCP by reacting CHP and α-CA in the presence of an acid catalyst, while continuously removing the formed water out of the reaction system, the reaction is carried out in the presence of a polar solvent.

The acid catalyst used in this invention includes conventional ones, for example, inorganic acids such as sulfuric acid, hydrochloric acid, perchloric acid and the like, and organic acids such as p-toluene sulfonic acid, trichloroacetic acid and the like.

It is desirable in this invention to adopt a conventional method in order to continuously remove the water formed in the reaction. An inactive gas, for example, nitrogen can be blown into the reaction system to distill off the water, such that the reaction is carried out under a reduced pressure to distill out the water, or the reaction can be carried out in the presence of a hydrocarbon such as hexane, benzene, toluene or the like co-existing in the reaction system to effect an azeotropic distillation of water.

Accordingly, it is desirable that the polar solvent used in this invention is one which is hardly distilled off with water during the above removal of water, and for this reason one which has a boiling point not lower than 120° C./760 mm Hg, is preferable.

As the polar solvent used in this invention, for example, hexamethylphosphoramide, 1,3-dimethyl-2-imidazolidinone, and any of the compounds shown in the following general formulae (1) to (IV), or the like are preferable.

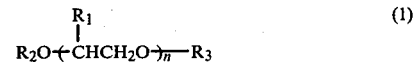

(1)

In the formula, $R_1$ represents a hydrogen atom or a methyl group, $R_2$ and $R_3$ represents a one hydrogen atom, an alkyl group having a carbon number of 1 to 4 or a phenyl group, and n is an integer of 1 to 10.

(II)

In the formula, $R_4$ represents an alkyl group having a carbon number of 1 to 4 or a phenyl group.

(III)

In the formula, $R_5$ represents an alkyl group having a carbon number of 1 to 4, a phenyl group or a benzyl group.

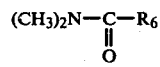

wherein $R_6$ represents a hydrogen atom or a methyl group.

Examples of the compounds of the general formula (I) are ethylene glycol, ethylene glycol monomethyl ether, ethylene glycol monoethyl ether, ethylene glycol monobutyl ether, ethylene glycol diethyl ether, ethylene glycol dibutyl ether, ethylene glycol monophenyl ether, diethylene glycol, diethylene glycol monomethyl ether, diethylene glycol monoethyl ether, diethylene glycol monobutyl ether, diethylene glycol dimethyl ether, diethylene glycol diethyl ether, diethylene glycol dibutyl ether, triethylene glycol, triethylene glycol monoethyl ether, tetraethylene glycol, polyethylene glycol, propylene glycol, propylene glycol monomethyl ether, propylene glycol monoethyl ether, propylene glycol monobutyl ether, propylene glycol mono-n-propyl ether, propylene glycol isopropyl ether, propylene glycol phenyl ether, dipropylene glycol, dipropylene glycol monomethyl ether, tripropylene glycol monomethyl ether, polypropylene glycol, and the like.

Examples of the compounds of formula (II) are triethyl phosphate, tributyl phosphate, triphenyl phosphate and the like.

Examples of the compounds of formula (III) are dimethyl sulfoxide, diethyl sulfoxide, dipropyl sulfoxide, dibutyl sulfoxide, diphenyl sulfoxide, dibenzyl sulfoxide, and the like.

As the compounds of formula (IV), N,N-dimethylformamide, N,N-dimethyl acetamide, and the like are exemplified as preferable ones.

When using these polar solvents, one of them may be solely used, or more than one of them may be used in combination.

The amount of the polar solvent to be used is preferably in the range of 0.5 to 30 times by mole equivalent based on the acid catalyst used. The use of an amount of the polar solvent less than 0.5 time by mole equivalent is not desirable, since such an amount is hardly effective to sufficiently suppress the acid-decomposition of DCP and to sufficiently raise the yield of DCP, while the use of an amount of more than 30 times by mole equivalent is also undesirable, since the formation reaction of DCP is considerably delayed by said amount resulting in an economic disadvantage.

The mole ratio of the starting materials, CHP and α-CA, which are used in this invention, is preferably in the range from 1 to 1.5 as α-CA/CHP ratio. A mole ratio of more than 1.5 or less than 1 is not desirable, because when the mole ratio is more than 1.5, the producing installation is largesized and the cost for recovering unreacted α-CA is more expensive, and further the separation of DCP tends to be more difficult. When said mole ratio is less than 1, the yield decreases.

The reaction temperature of this invention is within the range of 30° to 80° C., preferably 35° to 60° C.

The production process of DCP of this invention can be carried out either in a batch system, or a continuous flow system.

The above explained production process of DCP of this invention has characteristics as follows.

First, considerably safe operations can be attained in an industrial scale production of DCP, since the decomposition of CHP and DCP as seen in conventional processes does not substantially occur because of the existence of the polar solvent, though a strong acid is used as the catalyst.

In addition, DCP of good quality can be obtained in high yield, since the decomposition does not substantially occur, resulting in no or very little amount of decomposition products.

Furthermore, this process is advantageous in an economic sense, since the reaction is completed at a low temperature in a short time.

This invention is further illustrated in the following Examples in more detail.

The percentages mentioned in the Examples and Comparative Test are based on molarity.

EXAMPLE 1

In a four neck flask of 300 ml inner volume which was provided with a nitrogen gas blowing tube, a condenser, and a thermometer, there were charged 95 g (0.5 mole) of a 80% CHP, 76.3 g (0.55 mole) of a 98% α-CA, and 10.4 g (0.057 mole) of triethyl phosphate (b.p. 215.5° C./760 mm Hg). The content of the flask was reacted by slowly adding 5.7 g (0.0285 mole) of a 50% aqueous solution of sulfuric acid dropwise therein, while maintaining the temperature at 50° C. and passing nitrogen gas (2l/min) through the reaction system.

A part of the content was sampled at predetermined times and amounts of the active oxygen were measured to determine concentrations of CHP and DCP. From the respective resulting values, the conversion ratios of CHP and the selectivities for DCP, the selectivity meaning the portion (in %) of the reacted CHP was converted to DCP, were calculated. The obtained results are shown in Table 1.

After the reaction was maintained for 5 hours, the product was washed successively with a diluted alkaline aqueous solution and warmed water. Then, the resultant product was dehydrated and filtered to give a oily product, and then cooled to a temperature below 0° C. A pale yellow crude DCP having a melting point of 38° C. was obtained in an amount of 105 g.

Recrystallization of the crude DCP in methanol resulted in 94.5 g of white DCP having a melting point of 39°~40° C.

Gas-chromatographic analysis of this DCP gave a purity of 99.9%.

TABLE 1

| Reaction time (hrs) | Conversion ratio of CHP (%) | Selectivity for DCP (%) |
|---|---|---|
| 0.5 | 50.1 | 90.4 |
| 1.0 | 67.1 | 90.1 |
| 3.0 | 93.5 | 89.5 |
| 4.0 | 96.8 | 89.3 |
| 5.0 | 98.0 | 88.9 |

Comparative Test 1

The reaction was carried out according to the same procedures as those in Example 1, but excluding triethyl phosphate. An odor attributed to the decomposition of DCP and a remarkable increase in heat liberation were observed after 2.2 hours for the initiation of the reaction and then water was poured into the reaction mixture to stop the reaction.

The conversion ratios of CHP and the selectivities for DCP were determined during the 2.2 hours starting from the initiation of the reaction. Results are shown in Table 2.

TABLE 2

| Reaction time (hrs.) | Conversion ratio of CHP (%) | Selectivity for DCP (%) |
|---|---|---|
| 0.5 | 50.3 | 88.5 |
| 1.0 | 68.2 | 85.5 |
| 2.2 | 100 | 42 |

EXAMPLES 2 to 8

The respective reactions were carried out according to the same procedures as those in Example 1, except that the polar solvents listed in Table 3 were used in amounts of 0.057 mole each, instead of triethyl phosphate. The respective conversion ratios of CHP and the selectivities for DCP were determined after 5 hours from the initiation of the reaction in the same way as in Example 1. The obtained results are shown in Table 3.

TABLE 3

| Example No. | Polar solvent Compound | b.p. (°C./760 mm Hg) | Conversion ratio of CHP (%) | Selectivity for DCP (%) |
|---|---|---|---|---|
| 2 | Ethylene glycol | 197.85 | 97.4 | 89.0 |
| 3 | Ethylene glycol monophenyl ether | 244.7 | 98.2 | 88.6 |
| 4 | Diethylene glycol dibutyl ether | 254.6 | 98.1 | 88.5 |
| 5 | Polyethylene glycol (molecular weight 400) | — | 97.8 | 88.8 |
| 6 | Propylene glycol isopropyl ether | 187 | 97.6 | 88.8 |
| 7 | Tributyl phosphate | 289 | 97.9 | 89.1 |
| 8 | Triphenyl phosphate | 399 | 98.0 | 89.2 |

EXAMPLE 9

Into the same flask as used in Example 1, there were charged 95 g (0.5 mole) of 80% CHP, 76.3 g (0.55 mole) of a 98% α-CA and 17.9 g (0.10 mole) of hexamethyl phosphoramide (b.p. 235° C./760 mm Hg.).

Then, the content of the flask was reacted at 35° C. by adding 10 g of an acetic acid solution containing 7.18 g (0.05 mole) of a 70% perchloric acid, while introducing nitrogen gas therein.

A part of the content was sampled at predetermined time to determine the conversion ratio of CHP and the selectivities for DCP in the same way as in Example 1. The obtained results are shown in Table 4.

After continuing the reaction for 5 hours, the obtained product was treated in the same manner as in Example 1 to give 100.1 g of DCP as white fine particles. This DCP showed a melting point of 39°~40° C. and was of 100% purity.

TABLE 4

| Reaction time (hrs.) | Conversion ratio of CHP (%) | Selectivity for DCP (%) |
|---|---|---|
| 1.0 | 86.5 | 90.5 |
| 2.0 | 96.7 | 90.1 |
| 3.0 | 99.6 | 90.1 |
| 4.0 | 99.7 | 89.7 |
| 5.0 | 99.9 | 89.3 |

Comparative Test 2

The reaction was carried out in the same manner as in Example 9, except excluding hexamethyl phosphoramide.

However, after 2.1 hours from the initiation of reaction, remarkable heat generation was observed which caused bumping of the contents.

The organic material which remained in the flask in a very small amount, was analysed by the gas-chromatography.

The gas-chromatography analysis showed that the said organic material was almost all phenols and dimers of α-methyl styrene, while no DCP was detected. The conversion ratio of CHP and the selectivity for DCP were determined during 2 hours starting from the initiation of the reaction in the same ways as in Example 1. The obtained results are shown in Table 5.

TABLE 5

| Reaction time (hrs.) | Conversion ratio of CHP (%) | Selectivity for DCP (%) |
|---|---|---|
| 1.0 | 87.0 | 90.2 |
| 2.0 | 96.8 | 78.4 |

EXAMPLES 10 to 15

The respective reactions were carried out in the same manner as in Example 9, except that the charged amount of hexamethyl phosphoramid was changed to the amounts which are shown in Table 6. The respective conversion ratios of CHP and the respective selectivities for DCP after 4 hours from the initiation of the respective reactions were determined according to the same procedures as those described in Example 1.

The obtained results are shown in Table 6.

As Seen from Table 6, it was recognized that the selectivity for DCP was somewhat reduced for the reason that there occurred slight acid-decomposition of DCP when the molar ratio of hexamethyl phosphoramide to perchloric acid (hexamethyl) phosphoramide/perchloric acid) was less than 0.5 time as in Example 10. On the other hand it was recognized that the conversion ratio of CHP somewhat decreased when the molar ratio exceeded 30 times as in Example 15 for the reason that the reaction was a little retarded.

TABLE 6

| Example No. | Molar ratio of hexamethyl phosphoramide/perchloric acid (times) | Conversion ratio of CHP (%) | Selectivity for DCP (%) |
|---|---|---|---|
| 10 | 0.3 | 99.9 | 79.1 |
| 11 | 0.5 | 99.9 | 88.2 |
| 12 | 5.0 | 99.8 | 89.6 |
| 13 | 10.0 | 99.7 | 89.7 |
| 14 | 30.0 | 92.4 | 90.0 |
| 15 | 40.0 | 78.3 | 90.6 |

EXAMPLE 16

Into a flask of 500 ml inner volume which was provided with a stirrer, a thermometer and a vacuum system line, there were charged 95 g (0.5 mole) of a 80% CHP, 104.1 g (0.75 mole) of a 98% α-CA and 46.8 g (0.6 mole) of dimethyl sulfoxide. The content of the flask was reacted by slowly adding 30 g of an acetic acid solution containing 3.0 g (0.03 mole) of 98% sulfuric acid, under the pressure of 15 mm Hg, while maintaining the temperature thereof at 45° C. with stirring.

A part of the content was sampled at predetermined times and the conversion ratio of CHP as well as the selectivity for DCP were determined in the same way as in Example 1.

The obtained results are shown in Table 7.

Furthermore, after 7 hours from the initiation of the reaction, the product was treated in the same way as in Example 1 to give 103.7 g of DCP as white fine particles. The analyses carried out in the same way as in Example 1 showed that the DCP had a melting point of 39°~40° C. and a purity of 100%.

TABLE 7

| Reaction time (hrs) | Conversion ratio of CHP (%) | Selectivity for DCP (%) |
| --- | --- | --- |
| 0.5 | 48.3 | 92.6 |
| 1.0 | 64.7 | 92.2 |
| 3.0 | 90.2 | 91.8 |
| 5.0 | 93.0 | 91.4 |
| 7.0 | 98.0 | 90.0 |

Comparative Test 3

The reaction was carried out according to the same procedures as those described in Example 16, except that dimethylsulfoxide was not used.

After about 2.5 hours from the initiation of the reaction, remarkable heat generation was observed, whereupon the flask was cooled in an ice-water bath and further the reaction system was treated with water to cease the reaction.

The organic layer of the obtained reaction product was analyzed by a gas chromatography, thereby obtaining that the conversion ratio of CHP was 100% and the selectivity for DCP was 46.0%.

EXAMPLE 17 TO 22

Each reaction was carried out according to the same procedures as those described in Example 16, except that each polar solvent shown in Table 8 (0.6 mole for one polar solvent alone and 0.3 mole each respectively for a mixture of two or more polar solvents) was used in place of dimethylsulfoxide.

The conversion ratios of CHP and the selectivity for DCP at the fifth hour from the initiation of the reaction were measured respectively, according to the same procedures as those described in Example 1. The obtained results are shown in Table 8.

TABLE 8

| Example | Name of Compound | Polar solvent Quantity (mole) | Boiling point (°C./760 mm Hg) | Conversion ratio of CHP (%) | Selectivity for DCP (%) |
| --- | --- | --- | --- | --- | --- |
| 17 | Dipropylene glycol | 0.6 | 231.8 | 93.4 | 90.8 |
| 18 | Diethyl sulfoxide | 0.6 | *88~90 | 92.6 | 91.1 |
| 19 | N.N—dimethyl acetoamide | 0.6 | 166 | 92.0 | 90.3 |
| 20 | Hexamethyl phosphoramide | 0.3 | 235 | 93.7 | 91.5 |
|  | Dimethyl sulfoxide | 0.3 | 189 |  |  |
| 21 | Tributyl phosphate | 0.3 | 289 | 93.1 | 90.7 |
|  | Diphenyl sulphoxide | 0.3 | 340 |  |  |
| 22 | Propylene glycol monoethyl ether | 0.3 | 132.2 | 93.0 | 90.7 |
|  | Hexamethyl phosphoramide | 0.3 | 235 |  |  |

*a boiling point at 15 mm Hg

EXAMPLE 23

Into the same flask as used in Example 16, there were charged 95 g (0.5 mole) of a 80% CHP, 90.2 g (0.65 mole) of a 98% α-CA, 2.84 g (0.0087 mole) of triphenyl phosphate and 0.64 g (0.0087 mole) of N,N-dimethylformamide (boiling point 153° C./760 mm Hg,) and there further was charged 1.5 g (0.0087 mole) of p-toluenesulfonic acid.

The content of the flask was reacted at 15 mm Hg maintaining the same at a temperature of 55° C. with stirring.

At predetermined times, a part of the content of the flask was sampled, and the conversion ratio of CHP as well as the selectivity for DCP were estimated in the same way as described in Example 1.

The obtained results are shown in Table 9.

After 7 hours from the initiation of the reaction, the reacted product was handled according to the same procedures as in Example 1, to obtain 102.0 g of DCP in a white fine powder. The obtained DCP was analyzed according to the same procedures as those in Example 1. The melting point thereof was 39°~40° C. and its purity was 99.9%.

TABLE 9

| Reaction time (hrs) | Conversion ratio of CHP (%) | Selectivity DCP (%) |
| --- | --- | --- |
| 1.0 | 32.2 | 91.8 |
| 2.0 | 51.9 | 91.3 |
| 3.0 | 66.0 | 91.1 |
| 5.0 | 90.0 | 90.4 |

TABLE 9-continued

| Reaction time (hrs) | Conversion ratio of CHP (%) | Selectivity DCP (%) |
|---|---|---|
| 7.0 | 97.0 | 90.0 |

Comparative Test 4

The reaction was carried out according to the same procedures as those in Example 23, except that triphenyl phosphate and N,N-dimethylformamide were not used.

However, four hours after the reaction started, the content of the flask became coloured. At 5.5 hours later, the content of the flask became remarkably colored and remarkable heat generation was observed therein.

The obtained product was handled according to the same procedures as those in Example 1, whereby DCP of a white powder was not obtained but a yellow matter was obtained in a slurry.

The conversion ratios of CHP and the selectivities for DCP until to 5.5 hours from the initiation of the reaction were estimated in the same way as in Example 1.

The obtained results are shown in Table 10.

TABLE 10

| Reaction time (hrs) | Conversion ratio of CHP (%) | Selectivity for DCP (%) |
|---|---|---|
| 1.0 | 34.0 | 90.1 |
| 2.0 | 53.1 | 89.5 |
| 3.0 | 67.0 | 88.5 |
| 5.0 | 92.4 | 80.0 |
| 5.5 | 98.9 | 72.1 |

EXAMPLE 24

In the same flask as used in Example 1, there were charged 95 g (0.5 mole) of a 80% CHP, 78 g (0.55 mole) of a 96% α-CA and 10.3 g (0.09 mole) of 1,3-dimethyl-2-imidazolidinone (boiling point: 225.5° C./760 mm Hg). The content of the flask was reacted by slowly adding 30 g of an acetic acid containing 3.0 g (0.03 mole) of a 98% sulfuric acid, while flowing nitrogen gas therein at velocity of 2 l/min and keeping the temperature thereof at 55° C.

A part of the content was sampled at predetermined times and the conversion ratio of CHP as well as the selectivity for DCP were determined in the same way as in Example 1.

After 4 hours from the initiation of the reaction, the reacted product was handled according to the same procedures as those as Example 1, to obtain 96.8 g of DCP in white fine powder. The obtained DCP was analyzed according to the same procedures as those in Example 1. The melting point thereof was 39° C. to 40° C. and its purity was 99.9%.

The obtained results are shown in Table 11.

TABLE 11

| Reaction time (hrs) | Conversion ratio of CHP (%) | Selective rate for DCP (%) |
|---|---|---|
| 0.5 | 55.1 | 92.2 |
| 1.0 | 76.8 | 91.6 |
| 2.0 | 99.2 | 91.2 |
| 3.0 | 99.9 | 90.8 |
| 4.0 | 100.0 | 90.5 |

Comparative Test 5

The reaction was carried out, according to the same procedures as those in Example 24, except that 1,3-dimethyl-2-imidazolidinone was not employed.

After 2.0 hours from the initiation of the reaction, there was a decomposition smell of DCP and a remarkable heat generation was observed in the reaction system, such that water was added to the reaction system to cease the reaction.

The conversion ratios of CHP and the selectivities for DCP until 2.0 hours from the initiation of the reaction are shown in Table 12.

TABLE 12

| Reaction time (hrs) | Conversion ratio of CHP (%) | Selectivity for DCP (%) |
|---|---|---|
| 0.5 | 57.8 | 90.6 |
| 1.0 | 78.8 | 86.0 |
| 2.0 | 100.0 | 40.2 |

EXAMPLE 25 TO 30

The reactions were carried out according to the same procedures as those in Example 24, respectively except that the amounts of 1,3-dimethyl-2-imidazolidinone to be used were as shown in Table 13.

The respective conversion ratios of CHP and the selectivities for DCP until 2 hours after the initiation of the reaction are shown in Table 13.

TABLE 13

| Examples | 1,3-dimethyl-2-imidazolidinone sulphuric acid mole ratio (times) | Conversion ratio of CHP (%) | Selectivity for DCP (%) |
|---|---|---|---|
| 25 | 0.3 | 99.8 | 80.2 |
| 26 | 0.5 | 99.3 | 89.8 |
| 27 | 5.0 | 99.1 | 90.3 |
| 28 | 10.0 | 98.8 | 90.4 |
| 29 | 30.0 | 92.5 | 90.8 |
| 30 | 40.0 | 79.1 | 91.0 |

It is apparent from Table 13 that when the mole ratio of 1,3-dimethyl-2-imidazolidinone to sulphuric acid is less than 0.5 time (Example 25), the selectivity for DCP drops slightly because the acid decomposition of DCP occurs a little, and when said mole ratio is over 30 times, the conversion ratio of CHP drops slightly, because the reaction rate decreases slightly.

EXAMPLE 31

Into a flask of 300 ml inner volume which was provided with a stirrer, a thermometer and a vacuum system line, there were charged 95 g (0.5 mole) of a 80% CHP, 99.2 g (0.7 mole) of a 96% α-CA, 5.7 g (0.05 mole) of 1,3-dimethyl-2-imidazolidinone and 9.0 g (0.05 mole) of hexamethyl phosphoramide. Further, the content of the flask was reacted by slowly adding 10 g of an acetic acid solution containing 2.9 g (0.02 mole) of a 70% perchloric acid, maintaining the temperature thereof at 40° C. at under a pressure of 15 mm Hg while stirring.

At predetermined times, a part of the content of the flask was sampled. The conversion ratio of CHP and the selectivity for DCP in relation with the resulting product were determined.

The obtained results are shown in Table 14.

The resulting product was handled according to the same procedures as those in Example 1, thereby obtaining 104.0 g of DCP as white fine powder.

This DCP showed a melting point of 39°~40° C. and was of 99.9% purity.

TABLE 14

| Reaction time (hrs) | Conversion ratio of CHP (%) | Selectivity for DCP (%) |
|---|---|---|
| 0.5 | 57.8 | 92.1 |
| 1.0 | 78.1 | 91.4 |
| 2.0 | 99.3 | 91.0 |
| 3.0 | 99.9 | 90.7 |
| 4.0 | 100.0 | 90.5 |

EXAMPLES 32 TO 35

The respective reactions were carried out according to the same procedures as those in Example 31, except that the polar solvents as shown in Table 15 were used respectively.

The respective conversion ratios of CHP and the respective selectivities for DCP of the reaction system after two hours from the initiation of the reaction are shown in Table 15.

Comparative Test 6

The reaction was carried out in the same way as in Example 31, except that 1,3-dimethyl-2-imidazolidinone and hexamethyl phosphoramide were not used.

After 1.8 hours from the initiation of the reaction, a remarkable exothermic reaction was observed in the reaction system, such that water was poured into the flask to cease the reaction.

At that time, the conversion ratio of CHP was 100% and the selectivity for DCP was 37.2%.

TABLE 15

| Example | Polar solvent Name of Compound | Quantity (mole) | Conversion ratio of CHP (%) | Selectivity for DCP (%) |
|---|---|---|---|---|
| 32 | N,N—dimethyl formamide | 0.05 | 99.0 | 90.3 |
|  | 1,3-dimethyl-2-imidazolidinone | 0.05 | | |
| 33 | Triethyl phosphate | 0.05 | 99.1 | 90.8 |
|  | 1,3-dimethyl-2-imidazolidinone | 0.05 | | |
| 34 | Dimethyl sulfoxide | 0.05 | 98.9 | 91.0 |
|  | 1,3-dimethyl-2-imidazolidinone | 0.05 | | |
| 35 | Diethylene glycol | 0.05 | 99.1 | 90.1 |
|  | 1,3-dimethyl-2-imidazolidinone | 0.05 | | |

The embodiments of the invention in which an exclusive property or privilege is claimed are defined as follows:

1. In a process for producing dicumyl peroxide by reacting cumene hydroperoxide and α,α-dimethyl benzyl alcohol, in the presence of an acid catalyst, while continuously removing water which is formed in the reaction system therefrom, the improvement which comprises: the reaction is carried out at a temperature in the range of 30° to 80° C., in the presence of one or more polar solvents which are selected from the group consisting of hexamethyl phosphoramide, 1,3-dimethyl-2-imidazolidinone and compounds having the following formulae (I), (II), (III), and (IV):

$$R_2O+CHCH_2O)_n-R_3 \quad \text{with } R_1 \text{ on CH} \quad (I)$$

wherein $R_1$ is hydrogen or methyl, $R_2$ and $R_3$ each is hydrogen, alkyl having 1 to 4 carbon atoms, or phenyl, and n is an integer of from 1 to 10;

$$(R_4O)_3P=O \quad (II)$$

wherein $R_4$ is alkyl having 1 to 4 carbon atoms or phenyl;

$$(R_5)_2S=O \quad (III)$$

wherein $R_5$ is alkyl having 1 to 4 carbon atoms, phenyl or benzyl; and $$(CH_3)_2N-\underset{\underset{O}{\|}}{C}-R_6 \quad (IV)$$

wherein $R_6$ is hydrogen or methyl; and said acid catalyst is selected from the group consisting of sulfuric acid, hydrochloric acid, perchloric acid, p-toluene sulfonic acid and trichloroacetic acid.

2. A process for producing a dicumyl peroxide according to claim 1, wherein the mole ratio of said polar solvent to the said acid catalyst is in the range of 0.5 to 30 times.

3. A process for producing a dicumyl peroxide according to claim 1 or claim 2, wherein the mole ratio of the cumene hydroperoxide said α,α-dimethyl benzyl alcohol is in the range of 1 to 1.5.

4. A process according to claim 1, wherein the reaction temperature is in the range of 35° C. to 60° C.

5. A process according to claim 1, wherein said polar solvent has a boiling point not lower than 120° C. at 760 mm Hg.

6. A process according to claim 1, wherein said polar solvent is selected from the group consisting of ethylene glycol, ethylene glycol monomethyl ether, ethylene glycol monoethyl ether, ethylene glycol monobutyl ether, ethylene glycol diethyl ether, ethylene glycol dibutyl ether, ethylene glycol monophenyl ether, diethylene glycol, diethylene glycol monomethyl ether, diethylene glycol monoethyl ether, diethylene glycol monobutyl ether, diethylene glycol dimethyl ether, diethylene glycol diethyl ether, diethylene glycol dibutyl ether, triethylene glycol, triethylene glycol monoethyl ether, tetraethylene glycol, polyethylene glycol, propylene glycol, propylene glycol monomethyl ether, propylene glycol monoethyl ether, propylene glycol monobutyl ether, propylene glycol mono-n-propyl ether, propylene glycol isopropyl ether, propylene glycol phenyl ether, dipropylene glycol, dipropylene glycol monomethyl ether, tripropylene glycol monomethyl ether, polypropylene glycol, triethyl phosphate, tributyl phosphate, triphenyl phosphate, dimethyl sulfoxide, diethyl sulfoxide, dipropyl sulfoxide, dibutyl sulfoxide, diphenyl sulfoxide, dibenzyl sulfoxide, N,N-dimethylformamide, and N,N-dimethyl acetamide.

* * * * *